United States Patent [19]

Brown

[11] Patent Number: 5,766,951
[45] Date of Patent: Jun. 16, 1998

[54] SERUM-FREE MEDIUM SUPPORTING GROWTH AND PROLIFERATION OF NORMAL BONE MARROW CELLS

[75] Inventor: Ronald L. Brown, Derwood, Md.

[73] Assignee: Quality Biological, Inc., Gaithersburg, Md.

[21] Appl. No.: 974,783

[22] Filed: Nov. 12, 1992

[51] Int. Cl.$^6$ ........................................................ C12N 1/20
[52] U.S. Cl. .......................... 435/407; 435/404; 435/405; 435/406
[58] Field of Search .......................... 435/240.3, 240.31, 435/240.2, 240.21, 240.25, 404, 405, 406, 407

[56] References Cited

U.S. PATENT DOCUMENTS

| | | | |
|---|---|---|---|
| 4,135,975 | 1/1979 | Lichtman et al. | 435/240.3 |
| 4,560,655 | 12/1985 | Baker | 435/389 |
| 4,721,096 | 1/1988 | Naughton et al. | 435/240.3 |
| 4,762,792 | 8/1988 | Girgis et al. | 435/240.3 |
| 4,808,611 | 2/1989 | Cosman | 514/12 |
| 4,927,762 | 5/1990 | Darfler | 435/387 |
| 5,021,349 | 6/1991 | Drouet et al. | 435/407 |
| 5,061,620 | 10/1991 | Tsukamoto et al. | 435/7.21 |
| 5,232,848 | 8/1993 | Wolfe et al. | 435/240.31 |
| 5,397,706 | 3/1995 | Correa et al. | 435/240.31 |
| 5,409,825 | 4/1995 | Hoffman et al. | 435/384 |

FOREIGN PATENT DOCUMENTS 9201039  1/1992  WIPO.

OTHER PUBLICATIONS

Methods in Enzymology, vol. LVIII, edited by Jakoby et al., p. 213 (1979).
Miura et al. Proc. Int. Symp on Growth & Differentiation of Cells in Defined Environment, pp. 161–166 (1985).
Drouet et al., Br. J. Haematol., 73(2), pp. 143–147 (1989) (Biosis Abstract #89021847).
Flesch et al., Immunobiology, 171 (1–2) pp. 14–26 (1986) (Biosis Abstract #82060343).
Weiss et al., In Vitro, 16(7), pp. 616–628 (1980).
Bjare, U.. Pharmac. Ther., 53(3), pp. 355–374 (1992).
Jakoby et al., Methods of Enzymology vol. LVIII, published 1979 by Academic Press, "Media & Growth Requirements", pp. 44–93.
Jakoby et al, Methods of Enzymology, vol. LVIII, published 1979 by Academic Press, "The Growth of Cells in Serum-Free Hormone—Supplemental Media", pp. 94–109.
Kruse et al, Tissue Culture Methods & Applications, published 1973 by Academic Press, "Apparatus for Changing Tissue Culture Media", pp. 224–226.
Drouet, British Journal of Haematology, vol. 73, pp. 143–147 (1989).

*Primary Examiner*—Jean C. Witz
*Attorney, Agent, or Firm*—Birch, Stewart, Kolasch & Birch, LLP

[57] ABSTRACT

A serum-free medium which supports the growth and proliferation of bone marrow cells is described. Recipes for two formulations are given, one of which provides a medium suitable for growth of bone marrow cells for use in human therapeutic protocols.

22 Claims, No Drawings

SERUM-FREE MEDIUM SUPPORTING GROWTH AND PROLIFERATION OF NORMAL BONE MARROW CELLS

BACKGROUND OF THE INVENTION

The present invention relates to a serum-free medium which can support the growth and proliferation of normal bone marrow cells.

The growth of human bone marrow cells is becoming more important in view of recent developments of clinical regimens for combatting diseases such as cancer, myeloproliferative diseases and autoimmune diseases. However, many media are not suitable for culturing normal bone marrow cells. Therefore, a need exists for developing a serum-free medium which can support the growth and proliferation of bone marrow cells.

SUMMARY OF THE INVENTION

Since not all cells will proliferate in a single (universal) serum-free medium, care must be taken in the development of each medium. Such a medium is invaluable in the expansion of specific hematopoietic lineages for bone marrow transplantation. Such a medium will allow the potential to store small amounts of bone marrow (such as by freezing) and at a later time expand the cells by thawing the cells and growing them in vitro for transplantation purposes. The inventor has developed such a medium that can support bone marrow proliferation and in the presence of the appropriate cytokine, expand specific cell types/lineages.

Two serum-free media have been developed by the present inventor that support the proliferation of bone marrow cells. The bone marrow can be obtained from human, murine, sheep or other species. It is expected that the medium can support growth and proliferation of bone marrow cells from a broad range of mammalian species. Proliferation is enhanced and furthermore, differentiation can be induced by the addition of appropriate cytokines. The first medium (Example 1) is comprised of bovine proteins which renders it unsuitable for clinical purposes. Therefore a second medium (Example 2) was derived from U.S. Pharmaceutical grade components that will permit it to be used in clinical regimens.

Both media will support bone marrow proliferation, and the medium of Example 2 is comprised of U.S. Pharmaceutical grade reagents so that it can be used in clinical regimens.

It is accordingly one object of the present invention to provide a serum-free culture medium comprising a basal medium, glutamine, a mammalian serum albumin such as bovine serum albumin or human serum albumin, transferrin, a lipoprotein preparation which includes cholesterol, and insulin.

It is a second object of the invention to provide a serum free medium comprising glutamine, a serum-free preparation of a mammalian serum albumin such as bovine or human serum albumin, such trace cholesterol as is associated with albumin, transferrin and insulin in a basal medium. The basal medium is preferably Iscove's modified Dulbecco's Medium or another rich basal medium. This medium preferably does not contain a lipoprotein preparation such as EX-CYTE™ or other undefined components.

It is a third object of the invention to provide a method for growing cells from normal bone marrow which comprises cultivating said cells in a medium comprising a basal medium, glutamine, bovine serum albumin or human serum albumin, transferrin, a lipoprotein preparation including cholesterol, and insulin. It is a fourth object of the invention to provide a method for growing cells from normal human bone marrow which comprises cultivating said cells in a medium comprising a basal medium, glutamine, bovine serum albumin or human serum albumin, transferrin, such cholesterol as might be bound to the albumin, and insulin.

Various cytokines for driving proliferation and differentiation of the cells can optionally be added to the medium used to culture the cells. By means of adding various cytokines, the composition of the cell population can be altered with respect to the types of cells present in the population.

DETAILED DESCRIPTION OF THE INVENTION

In the art of tissue culture it has for some time been desired that a serum-free medium be found that supports the growth and proliferation of bone marrow cells. In part this is due to the desire of investigators to be able to study the effects of adding various components to a defined medium upon hematopoiesis. Also, therapeutic regimes are being developed which depend upon bone marrow transplant techniques. Such transplants are useful in the therapy of radiation exposure, immunodeficiency and tumors of the hematopoietic system (leukemias).

The media of the present invention, particularly that formulation suitable for use in human therapeutic protocols, has two types of utility in such transplant therapies. First, the media can be used in the expansion of specific bone marrow cells which are responsible for repopulating the host bone marrow. The media of the present invention can be used in the expansion of early progenitor cells which can then be mixed with fresh bone marrow and transplanted or transplanted alone. The rationale for this use is that the in vitro treatment allows for differentiation of the early progenitor cells to mature cells, capable of protecting the host from opportunistic diseases which occur during bone marrow transplantations.

In either of the above cases the presence of appropriate growth factors, such as interleukins (IL), colony stimulating factors (CSF), and the like, will influence the rate of proliferation and the distribution of cell types in the population of cells which results. Cytokines used for the expansion and differentiation of early progenitor cells are stem cell factor, interleukin-1 and interleukin-6. Cytokines used to stimulate proliferation and differentiation of mid-progenitor cells are interleukin-3 and granulocyte-macrophage colony stimulating factor. Cytokines which promote the differentiation of specific blood cell types are granulocyte colony stimulating factor, macrophage colony stimulating factor and erythropoietin. For transplantation purposes, the GM-colony forming cells are among the most important. The myeloid population is absolutely necessary for the transplant patient to survive. The role which each of these cytokines plays in hematopoiesis is under intense investigation in the art and it is expected that eventually it will be possible to faithfully recapitulate hematopoiesis in vitro.

The second utility is in "ex vivo purging" protocols. In a therapy of this type, "normal" bone marrow cells that are tainted with tumor cells, either of bone marrow or metastatic origin, are placed into in vitro culture in the medium of the present invention. The mixture of normal bone marrow cells and tumor cells is then treated with reagents which are preferentially cytotoxic for the tumor cells. Alternatively, the tumor cells can be selectively depleted from the culture using immobilized antibodies which specifically bind to the tumor cells. The "purged" bone marrow is then transplanted back into the patient.

The medium of the present invention is of course aqueous and is made using distilled water. The medium is formulated from freely soluble materials. Thus, the order of the addition of the ingredients is not particularly important to the invention. Typically, the basal medium is made first and the remaining components required for growth of bone marrow cells in the absence of serum are then added to the basal medium.

The basal medium is preferably Iscove's Modified Dulbecco's Medium (IMDM). Other basal media might be used, such as McCoy's 5a or a blend of Dulbecco's Modified Eagle's Medium and Ham's-F12 media at a 1:1 ratio. The requirements of the basal medium are that it provide i) inorganic salts so as to maintain cell osmolality and mineral requirements (e.g. potassium, calcium, phosphate, etc.), ii) essential amino acids required for cell growth, that is, amino acids not made by endogenous cellular metabolism, iii) a carbon source which can be utilized for cellular energy metabolism, typically glucose, and iv) various vitamins and co-factors, such as riboflavin, nicotinamide, folic acid, choline, biotin, and the like, as may be required to sustain cell growth.

The basal medium also typically contains a buffer to maintain the pH of the medium against the acidifying effects of cellular metabolism, usually bicarbonate or HEPES. The pH of the basal medium is usually between 6.8 and 7.2. The composition of IMDM is shown in Table I, below:

TABLE I

| Iscove's Modified Dulbecco's Medium | |
|---|---|
| Component | mg/L |
| L-Alanine | 25.0 |
| L-Arginine HCl | 84.0 |
| L-Asparagine.H$_2$O | 28.41$^D$ |
| L-Aspartic Acid | 30.0 |
| L-Cystine, disodium salt | 82.80 |
| L-Glutamic Acid | 75.0 |
| L-Glutamine | 584.0 |
| Glycine | 30.0 |
| L-Histidine HCl.H$_2$O | 42.0 |
| L-Isoleucine | 104.8 |
| L-Leucine | 104.8 |
| L-Lycine HCl | 146.2 |
| 1-Methionine | 30.0 |
| L-Phenylalanine | 66.0 |
| L-Proline | 40.0 |
| L-Serine | 42.0 |
| L-Threonine | 95.2 |
| L-Tryptophan | 16.0 |
| L-Tyrosine, 2Na.H$_2$O | 103.79 |
| L-Valine | 93.6 |
| Biotin | 0.013 |
| D-Ca Pantothenate | 4.00 |
| Choline Chloride | 4.00 |
| Folic Acid | 4.00 |
| i-Inositol | 7.00 |
| Nicotinamide | 4.00 |
| Pyridoxal HCl | 4.00 |
| Riboflavin | 0.40 |
| Thiamine HCl | 4.00 |
| Vitamin B$_{12}$ | 0.013 |
| Antibiotics | omitted |
| 2-a-Thioglycerol (7.5E-5M) | omitted |
| CaCl$_2$ (anhyd) | 165.0 |
| KCl | 330.0 |
| KNO | 0.076$^F$ |

TABLE I-continued

| Iscove's Modified Dulbecco's Medium | |
|---|---|
| Component | mg/L |
| MgSO$_4$ (anhyd) | 97.68$^B$ |
| NaCl | 4505. |
| NaH$_2$PO$_4$.H$_2$O | 125.0$^C$ |
| Na$_2$SeO$_3$.5H$_2$O | 0.0173$^D$ |
| Glucose | 4500. |
| Phenol Red | 15.0 |
| Sodium Pyruvate | 110.0 |
| NaHCO$_3$ | 3024. |
| HEPES 25 mM$^E$ | 5958. |
| CO$_2$ (The air in the jar over the medium contains 5% CO$_2$) | 5% |

$^A$Reference 1 lists L-Cystine, 22 mg/L, in addition to amounts in references 2 and 3.
$^B$Reference 3 lists MgSO$_4$.7H$_2$O and L-Tyrosine, 72 mg/L.
$^C$Value conforms with reference 2.
$^D$Reference 1 lists Na$_2$SeO$_3$, 0.0173 mg/L and L-Asparagine, 25 mg/L.
$^E$HEPES buffer is an integral component of the medium and osmolarity was corrected by the authors.
$^F$Reference 1 lists Fe(NO$_3$)$_3$.9H$_2$O; reference 5 replaces iron salt with KNO$_3$ as listed.

The additional factors added to the medium of the present invention are glutamine, albumin, transferrin, insulin and cholesterol. The glutamine concentration is between 100 and 500 μg/ml, preferably between 125 and 375 μg/ml and most preferably between 150 and 300 μg/ml. The concentration of bovine or human serum albumin is 1–8 mg/ml, preferably 3–4 mg/ml, most preferably 4 mg/ml; the transferrin concentration is between 20 and 200 μg/ml, more preferably 50–150 μg/ml, most preferably 100 μg/ml; the insulin concentration is between 0.025and 0.25 U/ml, more preferably 0.05–0.21 U/ml, most preferably 0.14 U/ml; the cholesterol concentration is 50 to 500 μg/ml, more preferably 50 to 150 μg/ml, most preferably 100 μg/ml. The cholesterol is preferably added as a component of EX-CYTE™ (Miles Laboratory) . EX-CYTE™ consists of cholesterol, lipoproteins and salt and is prepared as described in U.S. Pat. No. 4,762,792, hereby incorporated by reference. EX-CYTE™ is added at 200 μg/ml protein concentration so as to provide cholesterol at a concentration of 100 μg/ml. Alternatively, limited amounts of cholesterol can be added by use of serum albumin preparations. One finds that sufficient cholesterol remains bound to albumin, as it is typically prepared, to support the growth and proliferation of bone marrow cells in the media formulated as in the present invention. Lower amounts of cholesterol can be used in the medium if the medium is changed more frequently during the cultivation of cells.

All of the ingredients in the medium, including the ingredients in the basal medium, are present in amounts sufficient to support the growth and proliferation of cells from human bone marrow. If a basal medium is made which comprises IMDM reformulated with respect to the amounts of the components of IMDM, it is expected that the reformulation will contain those components in amounts 0.1-fold to 10-fold their amounts in the formulation IMDM.

The medium is formulated and sterilized in a manner conventional in the art. Typically, stock solutions of these components are made filter sterilized. A finished medium is usually tested for various undesired contaminants, such as mycoplasma or virus contamination, prior to use.

The invention is illustrated by the Examples below, which are not intended to be limiting of the scope of the invention.

EXAMPLE I

The serum-free medium of this example (SF-1) is composed of the basal medium, Iscove's Modified Dulbecco's Medium, supplemented with 2 mM glutamine, 100 U/ml penicillin, 100 µg/ml streptomycin and the serum-free components: bovine serum albumin (4 mg/ml) Cohn's Fraction V, fatty-acid free, Miles, Inc., iron-poor human transferrin (100 µg/ml) (Sigma or Miles, Inc.), sodium or zinc bound bovine insulin (0.14 U/ml) (Eli Lily) and bovine cholesterol (100 µg/ml; in the form of PENTEX®, EX-CYTES® III Growth Enhancement Media Supplement (liquid form) (Miles, Inc.), which is added at 200 µg/ml of protein).

Human bone marrow cells were obtained from consenting donors by aspiration from the posterior iliac crest. The cells were separated by centrifugation on Ficoll-Hypaque as well-known in the art. The "buffy coat" containing the mononuclear cells was pipetted from the gradient, washed twice in SF-1 and seeded at $1 \times 10^6$ cells/ml in SF-1 and incubated at 37° C. in an atmosphere of 5% $CO_2$ in air. At eight days the culture maintained a cell viability of $6.2 \times 10^5$ cells/ml. The addition of human recombinant IL-3 at 100 ng/ml did not alter the viability of the cells; $5 \times 10^5$ cells/ml (Table II) were stably maintained. However, the addition of the IL-3 expanded the number of GM colony forming cells from 338 to 1221 per ml using SF-1. Similar results using mouse bone marrow cells and murine recombinant IL-3 were obtained using SF-1 (Table III). These results illustrate that the medium will support the expansion of the GM-colony forming cells which are important in bone marrow cell transplantation.

TABLE II

The proliferation of human bone marrow cells using SF-1

| Day | SF-1 −IL-3 | SF-1 +IL-3 |
|---|---|---|
| 0 | $1.0 \times 10^6$ | $1.0 \times 10^6$ |
| 8 | $6.2 \times 10^5$ | $5.0 \times 10^5$ |

TABLE III

Expansion of GM-Colony forming cells by addition of IL-3 to SF-1 medium

| Species | GM-Colony forming cells/ml −IL-3 | GM-Colony forming cells/ml +IL-3 |
|---|---|---|
| human | 388 | 1221 |
| mouse | 25 | 241 |

EXAMPLE II

In order to develop a medium that can be used for human clinical bone marrow regimens, the components of SF-1 needed to be replaced with U.S. Pharmaceutical grade components. The serum-free medium of this example (SF-2) is composed of the basal medium IMDM, 2 mm L-glutamine, 100 U/ml penicillin, 100 µg/ml streptomycin and the serum free components: human injectable grade serum albumin (4 mg/ml) (Alpha Therapeutic Corp.), iron-poor human transferrin (100 µg/ml) (Sigma or Miles, Inc.) and zinc bound bovine insulin (0.14 U/ml) (Eli Lily). No cholesterol is added as such to the SF-2 medium, as no consistent source could be found that did not vary in quality from lot to lot. In order to circumvent the addition of cholesterol, the bone marrow cells need to be fed (i.e. the media is changed) every 4-7 days with fresh SF-2. This supports the growth of the bone marrow cells, presumably because the albumin contains a limited amount of bound cholesterol. Therefore, the periodic addition of fresh medium will compensate for the addition of any extra cholesterol. The medium can be changed every 1-7 days, preferably every 2-7 days, more preferably every 3-7 days and most preferably every 4-7 days. The medium is changed often enough to allow the normal bone marrow cells to grow and proliferate. Unnecessary changing of the media is avoided because of extra time and expense and risk of contamination.

To evaluate this hypothesis we compared the proliferation rates of rapidly proliferating murine bone marrow cells in SF-1 and SF-2 in the presence of murine recombinant stem cell factor (50 ng/ml) and murine recombinant GM-CSF (10 ng/ml). These factors readily stimulate the cells to proliferate to very high levels.

The data presented in Table IV illustrates that SF-1 and SF-2 supported the rapid proliferation of murine bone marrow cells in the presence of stem cell factor and GM-CSF to equivalent levels. In SF-1 and SF-2 (which each contained the growth factors) the cells proliferated from $1 \times 10^6$ cells/ml to $5.25 \times 10^6$ and $4.4 \times 10^6$ cells/ml, respectively, in seven days. The addition of fresh medium and growth factors supported the viability of the cells in SF-1 and SF-2 from day seven to day 10 to equivalent levels of $4.65 \times 10^6$ and $4.5 \times 10^6$ cells/ml, respectively. If the medium was not changed during this time, then the number of dead cells in SF-2 is twice as high as is found in SF-1.

TABLE IV

The proliferation of murine bone marrow cells in SF-1 and SF-2

| Day | SF-1 Viable cells | SF-2 Viable cells |
|---|---|---|
| 0 | $1.0 \times 10^6$ | $1.0 \times 10^6$ |
| 7 | $4.4 \times 10^6$ | $5.25 \times 10^6$ |
| 10 | $4.5 \times 10^6$ | $4.65 \times 10^6$ |

The formulations of SF-1 and SF-2 are compared in Table V, below:

TABLE V

Comparison of the components (per ml) of SF-1 and SF-2

| Components | SF-1 | SF-2 |
|---|---|---|
| Basal Medium | IMDM | IMDM |
| Folic Acid | 0 | 0 |
| Glutamine | 292 µg | 292 µg |
| Heparin | 0 | 0 |
| Hydrocortisone | 0 | 0 |
| Myoinositol | 0 | 0 |
| Monothioglycerol | 0 | 0 |
| BSA | 4 mg | 0 |
| HSA | 0 | 4 mg |
| Transferrin | 100 µg | 100 µg |
| Soy Bean Lecithin | 0 | 0 |
| Cholesterol | 0 | 0 |
| Insulin | 5.58 µg (0.14U) | 5.58 µg (0.14U) |
| EX-CYTE ™ | 200 µg* | 0 |

*200 µg/ml protein; provides 100 µg of cholesterol

The medium of the present invention has several advantages. First, the medium of the present invention, especially as embodied by SF-2, is useful in the growth of cells for human therapeutic protocols. Second, all of the components of the media of the present invention are freely soluble in water, making formulation of the medium very easy. No component need be prepared as a stock solution in an organic solvent, which upon dilution in the media might cause precipitation of some components.

The invention being thus described, various modifications of the materials and methods set forth will be obvious to one of skill in the art. Such modifications are within the scope of the invention as defined by the claims below.

LITERATURE CITED

The following references are cited within this paper. Each is hereby incorporated in its entirety by such reference.

1. N. N. Iscove and F. Meichers, J. Exp. Med. 147:923–933 (1978).
2. R. Dulbecco and B. Freeman, Virology 8:396–397 (1958).
3. R. Morton, In Vitro 6:89–108 (1970) (TCA Committee). p1 4. L. P. Rutzky and R. W. Pumper, In Vitro 9:466–469 (1974) (TCA Committee).
5. N. N. Iscove et al., Exp. Cell Res. 126:121–126 (1980).

What is claimed is:

1. A serum-free liquid culture medium, comprising:
   water;
   an effective amount of glutamine;
   an effective amount of human serum albumin having cholesterol bound thereto;
   transferrin in an amount of 50 to 200 µg/ml; and
   an effective amount of insulin,
   wherein said medium supports the growth of normal cells from human bone marrow, with the proviso that said medium does not contain lecithin, wherein all components of the medium are freely soluble in said water and wherein said medium is prepared solely from U.S pharmaceutical trade reagents.

2. The medium of claim 1, wherein the concentration of albumin is between 1 and 8 mg/ml.

3. A method for growing normal cells from human bone marrow which comprises:
   cultivating said cells in a liquid serum-free medium comprising:
   water;
   glutamine;
   1–8 mg/ml of a serum-free preparation of albumin from human serum;
   an effective trace amount of cholesterol provided by said serum-free preparation of albumin;
   an effective amount of transferrin; and
   insulin,
   wherein each of said glutamine, serum-free preparation of albumin, transferrin and insulin is dissolved in said waters, wherein said medium does not contain lecithin and wherein said medium is prepared solely from U.S. pharmaceutical grade reagents.

4. A method for growing normal cells from human bone marrow which comprises cultivating said cells in the medium of claim 1.

5. A method for growing normal cells from human bone marrow which comprises cultivating said cells in the medium of claim 1, wherein said medium further comprises at least one cytokine.

6. The method of claim 5, wherein said cytokine is selected from the group consisting of stem cell factor, interleukin-1, interleukin-3, interleukin-6, granulocyte-macrophage colony stimulating factor, granulocyte colony stimulating factor, macrophage stimulating factor and erythropoietin.

7. A method for growing normal cells from human bone marrow which comprises culturing said cells in the medium of claim 1, wherein said medium is replaced at intervals of 3–7 days.

8. A liquid serum free culture medium which supports the growth and proliferatioan of human bone marrow cells, comprising:
   water; and
   water soluble additives, wherein said water soluble additives include at least the following:
   an effective amount of glutamine, an effective amount of human serum albumin having cholesterol bound thereto, an effective amount of transferrin of at least 50 µg/ml, and an effective amount of insulin, wherein said medium supports the growth of normal cells from human bone marrow and wherein said medium does not contain lecithin and is prepared solely from U.S. pharmaceutical grade reagents.

9. A method for growing normal cells from human bone marrow which comprises cultivating said cells in said medium of claim 8.

10. The serum free culture medium of claim 8, which further comprises at least one cytokine.

11. A method for growing normal cells from human bone marrow which comprises cultivating said cells in said medium of claim 10.

12. A liquid serum-free culture medium which supports the growth of normal cells from human bone marrow for subsequent bone marrow transplantation, comprising:
   water;
   an effective amount of human serum albumin between 1 and 8 mg/ml with an effective amount of cholesterol bound thereto; and
   an effective amount of transferrin of at least 50 µg/ml;
   wherein said liquid serum-free culture medium does not contain lecithin and is prepared solely from U.S. pharmaceutical grade reagents.

13. A liquid serum-free culture medium which supports the growth of normal cells from human bone marrow, comprising:
   water;
   an effective amount of inorganic salts to maintain cell osmolality and mineral requirements;
   an effective amount of essential amino acids;
   an effective amount of glucose;
   an effective amount of vitamins and co-factors;
   a buffer;
   an effective amount of insulin;
   an effective amount of transferrin of at least 50 µg/ml; and
   an effective amount of cholesterol bound to a soluble carrier, wherein said medium does not contain lecithin and is prepared solely from U.S Pharmaceutical grade reagents.

14. A liquid serum-free liquid culture medium, comprising:
   water;
   an effective amount of albumin of at least 1 mg/ml;
   an effective amount of cholesterol bound to said albumin or to another soluble carrier;
   an effective amount of transferrin of at least 20 mg/ml; and an effective amount of insulin;

wherein said medium does not contain lecithin and supports the growth and proliferation of normal cells from human bone marrow.

15. The medium of claim 14, wherein said albumin is bovine serum albumin.

16. The medium of claim 14, which is made solely from U.S. pharmaceutical grade reagents.

17. A method for growing cells from human bone marrow which comprises cultivating said cells in the medium of claim 14, 15, or 16.

18. The medium of claim 5, wherein the cholesterol concentration is between 50 and 500 µg/ml.

19. The serum-free medium of claim 14, which comprises a lipoprotein preparation, wherein said lipoprotein preparation provides cholesterol in an amount of 50 to 500 µg/ml.

20. The serum-free medium of claim 12 or 13, which further comprises at least on cytokine.

21. The serum-free medium of claim 20, wherein said cytokine is selected from the group consisting of stem cell factor, interleukin-1, interleukin-3, interleukin-6, granulocyte-macrophage colony stimulating factor, granulocyte colony stimulating factor, macrophage stimulating factor and erythropoietin.

22. A method for expansion of human bone marrow cells which comprises cultivating human bone marrow cells in a medium prepared from U.S. pharmaceutical grade reagents according to claim 8, 10, 12, 13, 16, and expansion of specific hematopoietic lineages of said bone marrow cells for bone marrow transplantation.

* * * * *

UNITED STATES PATENT AND TRADEMARK OFFICE
CERTIFICATE OF CORRECTION

PATENT NO. : 5,766,951
DATED : June 16, 1998
INVENTOR(S) : Brown et al.

It is certified that error appears in the above-indentified patent and that said Letters Patent is hereby corrected as shown below:

Column 1, after the title, insert
--This invention was made with U.S. Federal Government support under Contract No. DK 42753-01 awarded by the National Institute of Diabetes and Digestive and Kidney Disease. The Government has certain rights in the invention.--

Signed and Sealed this

First Day of June, 1999

Attest:

Attesting Officer

Q. TODD DICKINSON

Acting Commissioner of Patents and Trademarks

UNITED STATES PATENT AND TRADEMARK OFFICE
CERTIFICATE OF CORRECTION

PATENT NO. : 5,766,951
DATED : June 16, 1998
INVENTOR(S) : Ronald L. BROWN

It is certified that error appears in the above-identified patent and that said Letters Patent is hereby corrected as shown below:

Column 8, Line 66:

Claim 14. Please change "20 mg/ml" to --20 µg/ml--

Signed and Sealed this

Twenty-eighth Day of September, 1999

Attest:

Q. TODD DICKINSON

*Attesting Officer*            *Acting Commissioner of Patents and Trademarks*